US008821855B2

(12) United States Patent
Jackson et al.

(10) Patent No.: US 8,821,855 B2
(45) Date of Patent: Sep. 2, 2014

(54) METHODS FOR ISOLATING PHAGE AND FOR CONTROLLING MICROORGANISM POPULATIONS WITH THE PHAGE

(75) Inventors: Lee E. Jackson, Layton, UT (US); Rex S. Spendlove, Millville, UT (US)

(73) Assignee: Omnilytics, Inc, Salt Lake City, UT (US)

( * ) Notice: Subject to any disclaimer, the term of this patent is extended or adjusted under 35 U.S.C. 154(b) by 0 days.

(21) Appl. No.: 12/027,209

(22) Filed: Feb. 6, 2008

(65) Prior Publication Data
US 2008/0124305 A1    May 29, 2008

Related U.S. Application Data

(62) Division of application No. 11/033,022, filed on Jan. 10, 2005.

(51) Int. Cl.
| C12N 7/01 | (2006.01) |
| A61K 35/76 | (2006.01) |
| A23B 4/20 | (2006.01) |
| C12N 7/00 | (2006.01) |
| A01N 63/00 | (2006.01) |
| A61K 35/74 | (2006.01) |
| C12N 15/00 | (2006.01) |

(52) U.S. Cl.
CPC . *A61K 35/76* (2013.01); *A23B 4/20* (2013.01); *C12N 7/00* (2013.01); *C12N 2795/00032* (2013.01); *A01N 63/00* (2013.01); *A61K 35/741* (2013.01)
USPC ..................................... 424/93.6; 435/235.1

(58) Field of Classification Search
CPC ................................................... A61K 35/76
USPC ............................................. 435/5; 424/93.1
See application file for complete search history.

(56) References Cited

U.S. PATENT DOCUMENTS

| 4,375,734 | A | 3/1983 | Kozloff et al. |
| 4,828,999 | A | 5/1989 | Jackson |
| 5,132,221 | A | 7/1992 | Ward et al. |
| 5,366,891 | A | 11/1994 | Premuzic et al. |
| 5,447,836 | A | 9/1995 | Wolber et al. |
| 5,811,093 | A | 9/1998 | Merril et al. |
| 6,207,411 | B1 | 3/2001 | Ross et al. |
| 6,699,701 | B1 * | 3/2004 | Sulakvelidze et al. ..... 435/235.1 |
| 2004/0029250 | A1 | 2/2004 | Sulakvelidze et al. |

FOREIGN PATENT DOCUMENTS

| WO | WO 87/02702 | 5/1987 |
| WO | WO 95/27043 | 10/1995 |
| WO | WO 98/08944 | 3/1998 |
| WO | 03/080823 A2 | 10/2003 |

OTHER PUBLICATIONS

Norris et al. Gene Therapy 2000, vol. 7, No. 9, pp. 723-725.*
Duplessis et al. Molecular Microbiology 2001, vol. 41, No. 2, pp. 325-336.*
Merril et al. Proc. Natl. Acad. Sci. USA, 1996, vol. 93, pp. 3188-3192.*
Gooden et al. Applied and Environmental Microbiology, 2003, vol. 69, No. 8, pp. 5032-5036.*
Bowen R. Jul. 2, 1999, Vitamins, pp. 1-2.*
Smith et al. Journal of General Microbiology, 1987, vol. 133, pp. 1111-1126.*
Mizoquchi et al. Appl. Environ Microbiol. 2003, vol. 69 (1), pp. 170-176.*
International Search Report for International Application No. PCT/US06/00854 dated Jul. 20, 2006 (2 pages).
Jacobs et al., "Genetic Complementation by Cloned Bacteriophage T4 Late Genes," Journal of Virology, vol. 39, No. 1, (Jul. 1981), pp. 31-45.
Doherty et al., "Dissecting the Host Response to a Gamma-Herpesvirus," The Royal Society, Phil. Trans. R. Soc. Lond. B. (2001), vol. 356, pp. 581-593.
Bergh et al., "High Abundance of Viruses Found in Aquatic Enyionments," Nature, vol. 340 (Aug. 10, 1989), pp. 467-468.
Demuth et al., "Direct Electron Microscopy Study on the Morphological Diversity of Bacteriophage Populations in Lake Plußsee," Applied and Environmental Microbiology, vol. 59, No. 10 (Oct. 1993), pp. 3378-3384.
Reanney et al., "The Ecology of Viruses Attacking Bacillus Stearothermophilus in Soil," Soil Biology Biochemistry, vol. 5 (1973), pp. 399-408.
Gautier et al., "Occurrence of Propionibacterium Freudenreichii Bacteriophages in Swiss Cheese," Applied and Environmental Microbiology, vol. 61, No. 7 (Jul. 1995), pp. 2572-2576.
Dhillon et al., "Studies on Bacteriophage Distribution: Virulent and Temperate Bacteriophage Content of Mammalian Feces," Applied and Environmental Microbiology, vol. 32, No. 1 (Jul. 1976), pp. 68-74.
Osawa et al., "Distribution of Ribonucleic Acid Coliphages in Animals," Applied and Environmental Microbiology, vol. 41, No. 1 (Jan. 1981), pp. 164-168.
Webpage, "New Method of Treatment May Reduce Contamination of Retail Poultry," www.eurekalert.org/pub_releases/2003-10/asfm-tft101503.php, 2003 (1 page).
Webpage, "Comparison of Methods for Beef Carcass Decontamination," http://micro312.tamu.edu/castillo/iamfes97.htm, Dec. 19, 1997 (1 page).

(Continued)

*Primary Examiner* — Bao Li
(74) *Attorney, Agent, or Firm* — Durham Jones & Pinegar Intellectual Property Law Group

(57) ABSTRACT

A lytic virus specific for a target strain of a microorganism and substantially free of undesirable genes may be utilized in processes including control of populations of microorganisms. The virus may include a host-range mutant, or "h-mutant." A method for generating virus includes growing virus-resistant variants of a target strain of a microorganism in the presence of viruses that are specific for the target strain. Only h-mutant viruses will proliferate. Wild-type virus-resistant and virus-resistant variants of a microorganism are also disclosed, as are methods generating such variants. Methods for controlling target strain microorganisms include introducing virus into a treatment site where control of a population of a target strain microorganism is desired or introducing virus-resistant variants of a microorganism into treatment sites where the presence of the microorganism is desired.

15 Claims, No Drawings

(56) References Cited

OTHER PUBLICATIONS

Webpage, "Lactic Acid as a Decontaminant in Slaughter and Processing Procedures," http://www.ncbi.nlm.nih.gov/htbin-post/Entrez/query?uid=4071948&form=6&db=m&Dopt=b, Dec. 19, 1997 (1 page).

Webpage, Microbiologic Evaluation of Carcasses Before and After Washing in a Beef Slaughter Plant, http://www.ncbi.nlm.nih.gov/htbin-post/Entrez/query?uid=7632246&form=6&db=m&Dopt=b, Dec. 19, 1997 (1 page).

Chakrabarty, A.M, Microbial Degradation of Toxic Chemicals: Evolutionary Insights and Practical Considerations, ASM News, 1996, pp. 130-137, vol. 62, No. 3, American Society of Microbiology, Washington D.C.

World Health Organization, Geneva, The World Health Report 1996, Fighting disease, Fostering Development, 138 pp.

Hagens, Steven, et al., "Therapy of Experimental Pseudomonas Infections with a Nonreplicating Genetically Modified Phage," Antimicrobial Agents and Chemotherapy, vol. 48, No. 10, Oct. 2004, pp. 3817-3822.

Merril, Carl R., et al., "Long-circulating bacteriophage as antibacterial agents," Proc. Natl. Acad. Sci. USA, vol. 93, Apr. 1996, pp. 3188-3192.

Broxmeyer, Lawrence, et al., "Killing of *Mycobacterium avium* and *Mycobacterium tuberculosis* by a Mycobacteriophage Delivered by a Nonvirulent *Mycobacterium*: A Model for Phage Therapy of Intracellular Bacterial Pathogens," Journal of Infectious Diseases, vol. 186, Oct. 15, 2002, pp. 1155-1160.

Sulakvelize, Alexander, et al., "Minireview, Bacteriophage Therapy," Antimicrobial Agents and Chemotherapy, vol. 45, No. 3, Mar. 2001, pp. 649-659.

Biswas, Biswajit, et al., "Bacteriophage Therapy Rescues Mice Bacteremic from a Clinical Isolate of Vancomycin-Resistant *Enterococcus faecium*," Infection and Immunity, vol. 70, No. 1, Jan. 2002, pp. 204-210.

Yoong, Pauline, et al., "Identification of a Broadly Active Phage Lytic Enzyme with Lethal Activity against Antibiotic-Resistant *Enterococcus faecalis* and *Enterococcus faecium*," Journal of Bacteriology, vol. 186, No. 14, Jul. 2004, pp. 4808-4812.

Akatov et al. J. Chemotherapy 1991, vol. 3, No. 5, pp. 275-278.

Schwarz et al. Mol. Gene. Genet 1981, vol. 183, pp. 181-186.

Rawling et al., Molecular Genetics of *Thiobacillus ferrooxidans*, Microbiological Reviews, 1994, vol. 58, No. 1, pp. 39-55.

English et al., "Use of Electroporation to Generate Thiobacillus neapolitanus Carboxysome Mutant," Applied and Environmental Microbiology, 1995, vol. 61, No. 9, pp. 3256-3260.

Broxmeyer et al., J. Infectious Diseases 2002, vol. 186, pp. 1155-1160.

Duplessis et al., Molecular Microbiology 2001, vol. 41, No. 2, pp. 325-336.

Marzari et al., Gene 1997, vol. 185, pp. 27-33.

European Patent Office, "Supplementary European Search Report", issued Sep. 6, 2012, in related European application No. EP 06 71 7987.

Paul A. Barrow, et al. "Bacteriophage therapy and prophylaxis: rediscovery and renewed assessment of potential" Trends in Microbiology, Elsevier Science Ltd., Kidlington, GB, vol. 5, Jan. 1, 1997, pp. 268-271, XP000993117, ISSN: 0966-842X, DOI: 10.1016/S0966-842X(97)01054-8.

\* cited by examiner

METHODS FOR ISOLATING PHAGE AND FOR CONTROLLING MICROORGANISM POPULATIONS WITH THE PHAGE

CROSS-REFERENCE TO RELATED APPLICATION

This application is a divisional of application Ser. No. 11/033,022, filed Jan. 10, 2005, pending, the entire disclosure of which is hereby incorporated herein by this reference.

TECHNICAL FIELD

The invention relates to viruses which control and prevent growth of harmful microorganisms and to processes which employ such viruses. It also relates to protection of helpful microorganisms from virus attack. In particular, the viruses of the present invention lack genes for virulence factors, toxins, antibiotic resistance, and other undesirable genes, and include host-range (h-mutant) viruses which are specific for wild-type virus-resistant strains of targeted microorganisms. More specifically, viruses of the present invention are lytic, thus they control and prevent further growth of harmful microorganisms that infect animals or plants by destroying these microorganisms. Such viruses may also be employed to develop and select strains of beneficial microorganisms which are resistant to wild-type and h-mutant viruses.

BACKGROUND

Viruses are known to alter populations of microorganisms, such as bacteria, fungi, algae, and protozoa. It has been estimated that, in nature, as many as one-third of all bacteria may be attacked by viruses each day. The destruction of microorganisms by viruses results in fluctuations of microbial populations in the environment, which is referred to as "cycling" of microbial populations. For example, populations of microorganisms increase in concentration until viruses contact and infect susceptible microorganisms, which are referred to as host microorganisms or "hosts." Viral infections of microorganisms decrease the number of available susceptible host microorganisms, and correspondingly increase the number of viruses. Without hosts to infect, many viruses are eventually destroyed by exposure to natural elements, such as ultraviolet light from the sun and enzymes in the environment. Thus, virus numbers decline, while host microorganism populations consequently increase. Such cycling of microbial populations in nature is common. Although it is somewhat difficult to detect and study viruses that attack microorganisms other than bacteria, those of skill in the art are aware that all populations of microorganisms (e.g., algae, rickettsiae, fungi, mycoplasmas, protozoas) are controlled and cycled in a similar manner by viruses that are capable of infecting and destroying such microorganisms.

Bacterial viruses, which are also referred to as "bacteriophages" or "phages," are ubiquitous and can be isolated from all bacterial populations where hosts can be cultivated and used for isolation. Phages are naturally occurring entities that are found in or on animals (including humans), plants, soil, and water. Viruses which infect algae, molds, mycoplasmas, protozoa, rickettsiae, yeasts, and other microorganisms are also known.

Two methods are typically employed in order to determine the concentration, which is also referred to as "quantification," of viruses in natural environments. First, electron microscopy may be used to visualize and count total viral particles in a sample of known size. Second, viable viruses may be cultured, or grown, and counted. An exemplary method of quantification by culturing and counting includes a technique which is typically referred to as a plaque assay. In plaque assays, the viruses that are to be quantified are mixed with a predetermined concentration of host cells and transferred to a liquid (e.g., buffer, mineral salts diluent, or broth). The mixture is then transferred to a semisolid growth medium. The concentration of host cells must be sufficiently great to form a confluent layer, which is typically referred to as a "lawn," in the semisolid growth medium as the cells grow. During incubation of the phage-host mixture, many of the viable viruses infect host cells. Subsequently, new viruses are produced within infected host cells, which are eventually destroyed, or "lysed," so that new viruses may be released therefrom. The new viruses then attack and eventually lyse cells that are adjacent to host cells from which the new viruses were released. This spread of infection, which continues as long as host cells are metabolizing, results in formation of clear areas, which are typically referred to as "plaques," in the host cell lawn. The number of viruses that were present in the original mixture is determined by counting the number of plaques that are formed in the host cell lawn. Accordingly, viruses that are quantified by this method are referred to as plaque-forming units ("PFU").

In order to quantify all of the various types of viruses in an environmental sample by culturing host cells and counting PFUs, host cells for each of the different viruses in the sample must be cultured. Many types of microorganisms in a given environmental sample are not known. Some of the known microorganisms cannot be cultivated. Therefore, the number of viruses that are present in a given environment may be underestimated when quantified by culturing and counting. Although it is estimated that one gram of soil includes as many as $10^8$ to $10^9$ microorganisms, quantification techniques such as direct plate counting, selective isolation, microscopy, and reassociation kinetics of total DNIA isolated from soil suggest that only a very small percentage of these microorganisms can be cultured. Thus, the development and application of direct electron microscopic counting methods have provided a better understanding of the number of viruses that are present in various environments, as well as the impact that viruses have in reducing microbial populations.

Phages have been quantified in water. Bergh et al. (1989), High abundance of viruses found in aquatic environments, Nature 340:467, used electron microscopy to determine the total concentration of bacterial viruses in a natural, unpolluted Norwegian lake. Phage concentrations of up to about $2.5 \times 10^8$ phages/ml were found in the water. Bacterial counts were as high as about $1.5 \times 10^7$ cells/ml. From these relative concentrations of phage and bacteria, it was estimated that as many as one-third of the bacterial population experiences one or more phage attacks each day. Similarly, Demuth et al. (1993) Direct electron microscopy study on the morphological diversity of bacteriophage populations in Lake Plussee, Appl. Environ. Microbiol. 59:3378, determined that phage levels in a German lake without sewage influences were as high as about $10^8$ phages/ml of lake water. As many as eleven morphologically different phages were identified in the water samples.

Phages have also been quantified in soil. Using the culturing and counting method, with *Bacillus stearothermophilus* as the host cell, Reanny, D. C. and Marsh S. C. N. (1973). The ecology of viruses attacking *Bacillus stearothermophilus* in soil Soil. Biol. Biochem. 5:399, reported that, on average, about $4.0 \times 10^7$ PFUs that would infect *B. stearothermophilus* were present in a gram of soil. Only phages against a single host were, however, quantified in the Reanny and Marsh study. Thus, had other bacterial hosts been tested along with *B. stearothermophilus*, or had electron microscopy quantification techniques been employed, phage counts would probably have been much higher.

Phages are also present in foods. Kennedy et al. (1986) Distribution of coliphages in various foods. J. Food Protect. 49:944, found *Escherichia coli* and phages that attack *E. coli* ("coliphages"), in 11 of 12 tested foods, each of which are available in many retail markets. For example, all ten ground beef samples tested by Kennedy et al. were contaminated with coliphages. Coliphages were also present in samples of fresh chicken, fresh pork, fresh oysters, fresh mushrooms, lettuce, chicken pot pie, biscuit dough, deli loaf deli roasted turkey and packaged roasted chicken. Similarly, Gautier et al. (1995) Occurrence of *Propionibacterium freudenreichii* bacteriophages in Swiss cheese, Appl. Environ. Microbiol. 61:2572, detected *Propionibacterium freudenireichii* phage concentrations of about $7 \times 10^5$ PFU/g in Swiss cheese.

Both undesirable and beneficial microorganisms are present in the environment. Viruses infect and destroy both beneficial and undesirable microorganisms. Soil microorganisms that enhance plant growth and microorganisms that degade toxic substances are exemplary of beneficial microorganisms in the environment. Undesirable microorganisms include pathogenic microorganisms and algae that cause algal blooms and fish kills.

In addition to naturally occurring microbial populations, in recent decades disease-causing microorganisms resistant to antibiotics have become epidemic in many hospitals, and have been notoriously difficult to control. During the past fifty or more years, the widespread use of antibiotics has resulted in the selection of antibiotic-resistant bacterial strains. *Staphylococcus aureus, Streptococcus pneumoniae, Streptococcus pyogenes, Enterococcus faecalis, Salmonella typhi, Hemophilus ducreyi, Hemophilus influenzae, Mycobacterium tuberculosis, Neisseria gonorrhoeae, Pseudomonas aeruginosa*, various *Shigella* species, members of the *Enterobacteriaceae* and *Pseudomonas* families, and other bacterial species are resistant to many of the conventionally employed antibiotics. Infections that are acquired during hospitalization, which are typically referred to as nosocomial infections, cause an estimated 60,000 deaths per year, and require treatment, which has been estimated to cost about $4.5 billion per year recently.

Statistics from the Centers for Disease Control and Prevention (CDC) indicate that the majority of nosocomial infections are caused by *E. coli, S. aureus*, coagulase-negative staphylococci, enterococci, pneumococci, and pseudomonads. In addition, according to the 1996 World Health Organization (WHO) annual report, "drug-resistant strains of microbes have evaded common treatments for tuberculosis, cholera, and pneumonia."

Consequently, the occurrence of infections that are caused by antibiotic-resistant bacteria has steadily increased in hospitals localized communities, and at-risk populations worldwide since the 1940s, shortly after antibiotics were first used for treating bacterial infections. For example, in 1941 practically all strains of *S. aureus* throughout the world were susceptible to penicillin G. By 1944 however, some strains of *S. aureus* were capable of making penicillinase, which is also typically referred to as β-lactamase, which degrades penicillin. In 1996, some strains of *S. aureus* were not only resistant to various forms of penicillin, but also to six of the seven other antibiotics that are conventionally used to treat *S. aureus* ("staph") infections.

1) Since 1988, the potential for selection of vancomycin-resistant mutants was a concern in that such resistance had been identified in Gram-positive bacteria, such as vanconmycin-resistant *E. faecalis*, or *faecium* ("VREF"); VEEF are also of great concern to health care professionals due to their deadly combination of antibiotic resistance, rapid spread, and high mortality rates in patients with VREF-associated infections.

2) Infections by methicillin-resistant *S. aureus* ("MRSA") pose an especially serious public health threat. MRSA typically display various patterns of multiple-drug resistance (i.e., are resistant to multiple types of antibiotics). Many strains of MRSA are susceptible only to the antibiotic vancomycin.

3) Although new and alternative drugs for treating infections of antibiotic-resistant strains of bacteria have been developed and discovered, many bacteria also develop resistance to such new and alternative drugs. For example, certain MRSA strains quickly developed resistance to the antibiotic ciprofloxacin. Moreover, in 1997, a strain of *S. aureus* was isolated from an infection that resisted 29 days of vancomycin treatment. To put the threat posed by this *S. aureus* strain in perspective, this *S. aureus* strain was categorized by the CDC as having intermediate resistance somewhat short of full resistance, and was labeled a medical red alert. It was reported that if MRSA strains which have resistance to vancomycin develop, death rates for all surgeries, including elective surgeries, may increase.

4) In 2001 the isolation of MRSA from three heart patients at McKay-Dee Hospital in Ogden, Utah, resulted in closure of its cardiac surgical units to all but emergency surgeries. Subsequently, vancomycin-resistant *S. aureus* (VRSA) have been isolated from clinical patients in Michigan (2002), Pennsylvania (2003) and New York (2004).

Similarly, about half of the known strains of *S. pneumoniae* are resistant to penicillins, which have conventionally been employed as the initial and primary treatment for *S. pneumoniae* infections. Some *S. pneumoniae* strains are resistant to cephalosporin antibiotics, which have conventionally been employed as a secondary treatment for *S. pneumoniae* infections. Penicillin and cephalosporin-resistant *S. pneumoniae* strains may be treated with vancomycin. The use of vancomycin, however, is undesirable because of severe side effects that vancomycin has on many patients and the possibility that vancomycin-resistant strains of *S. pneumoniae* may emerge.

The problem of antibiotic resistance is further compounded by the fact that microorganisms may transfer genetic information, which is referred to as "genes" or "DNA" for simplicity. Methods by which microorganisms, such as bacteria, can transfer DNA, and even entire genes, include conjugation, transformation, and transduction. Various genes, including genes that impart bacteria with resistance to antibiotic drugs, may be transferred from a first, or donor, microorganism to a second, or recipient, microorganism. In addition to transferring genes for antibiotic resistance, microorganisms may transfer genes that enable a microorganism to produce toxins, which are typically harmful to an infected host. Virulence factors, which determine the types of hosts and host cells that a microorganism can infect may also be transferred from one microorganism to another.

In conjugation, plasmid or chromosomal DNA is transferred directly from a donor microorganism to a recipient microorganism by means of specialized pili or "sex pili," which are small, hollow, filamentous appendages, which bind to and penetrate the cell membranes of recipient microorganisms. Conjugation is a process by which genes that code for antibiotic resistance in the "donor" microorganism pass to a recipient microorganism, transforming the recipient into an antibiotic-resistant microorganism.

Transformation is the transfer of DNA that has been released into the environment by a donor microorganism and incorporated by a recipient microorganism. Transformation experiments have been conducted in sterile soil that was inoculated with two parental strains of *Bacillus subtilis* with differentially marked, or tagged, DNA. Bacteria were isolated which carried the markers of both parental strains. Even under the best laboratory conditions, however, transformation is relatively inefficient and requires high densities of donor DNA and recipient cells. Conditions that would permit transformation in many microorganisms are typically not present in a natural, or uncontrolled, environment. Consequently, transformation is typically perceived as a laboratory phenomenon.

Transduction is the transfer of host genes to recipient microorganisms by viruses, such as phages. There are two kinds of phages, virulent, or lytic, and temperate. When a host cell is infected with a virulent phage, new phages, which are typically referred to as progeny, are grown in the host cell, and the host cell is subsequently lysed, or destroyed, so that the progeny may be released. In contrast, temperate phages typically infect host cells without destroying their host. Following infection of a host cell, temperate phages typically incorporate their genetic information into the DNA of the host cell. Many temperate phage-infected host cells can be subsequently induced, by ultraviolet light, mutagens, or otherwise, to enter a lytic cycle, wherein genetic information of the temperate phage produces progeny which then lyse the host cell.

Transduction of host DNA may be either "specialized" or "generalized." In specialized transduction, a temperate phage's genome is integrated into the chromosome of a host donor microorganism without lysing the host. The phage genome that was inserted into the host chromosome is referred to as a "provirus," or "prophage," and is passively replicated as the host cell and its chromosome replicate. Bacteria that carry proviruses are said to be lysogenic. Certain events, such as exposing the host microorganism and the provirus to ultraviolet light, may cause the provirus to act as a virulent phage, whereby the provirus is excised from the bacterial chromosome. Such excised proviruses may carry bacterial genes, or "donor" genes, with them. Upon infecting a new host, or recipient microorganism, these "donor" genes may be expressed, which may alter the phenotype, or physical gene expression, of the recipient microorganism.

Temperate and, possibly, some virulent phages may affect generalized transduction. During viral replication, a section of DNA of the donor microorganism, which is referred to as a "donor" gene, rather than the phage genome, may be enclosed inside a phage head. Phages that include only DNA of a host microorganism are referred to as transducing particles. A typical phage is only capable, however, of containing about one percent of the chromosome of a host, or "donor," microorganism. Thus, the simultaneous transfer of more than one gene by a single transducing particle is unlikely. Since transducing particles do not include a phage genome, transducing particles cannot produce progeny upon infecting a recipient microorganism. Instead, the donor gene has to be incorporated into the chromosome of the recipient microorganism. If the recipient microorganism is infected with only one transducing particle, it will survive and its phenotype may be altered by the integrated donor gene. It is very important to remember if the multiplicity of infection ("MOI") of transducing particles per recipient microorganism is high, the cell will probably be destroyed, which is typically referred to as "lysis from without."

The transfer of genetic information from one microorganism to another may have beneficial or undesirable effects. For example, a beneficial transfer of genetic information was disclosed by Chakrabarty, A. M. (1996) Microbial degradation of toxic chemicals; Evolutionary insights and practical considerations, ASM News 62:130. Microorganism-rich soil was introduced into a chemostat which contained a single industrial pollutant as a nutrient. In less than a year, pseudomonads which had acquired all of the enzymes needed to degrade the pollutant were isolated from the soil.

Similarly, genes that exhibit undesirable traits may also be transferred. Examples of such detrimental gene transfer include transfer of genes carrying resistance to antibiotics, and genes that code for production of toxins, such as shiga, diphtheria, and botulism toxins. Outbreaks of toxin-related diseases, such as toxic shock syndrome in 1980, the "flesh-eating streptococci" of 1994, and illnesses caused by *E. coli* 0157:H7 in undercooked hamburger, have been traced to the transfer of toxin genes by temperate phages. Genes that code for cholera toxin are also reported to have been transmitted by a temperate phage, which created yet another epidemic strain, *Vibrio cholerae* 0139.

Viruses have been isolated and employed in treating various types of bacterial infections. U.S. Pat. No. 4,375,734, which issued to Kozloff et al. on Mar. 8, 1983 ("Kozloff"), discloses use of a wild-type phage, Erh1, for protecting plants against frost injury caused by an ice nucleation-promoting bacterium, *Erwinia herbicola*. The treatment of corn plants with Erh 1 reduced the incidence of ice nucleation damage by about 20% to 25%. Kozloff et al. also discloses that Erh1 killed only about 90% of cultured *E. herbicola*, which suggests that some of the remaining 10% were resistant to wild-type Erh1.

U.S. Pat. No. 4,828,999, which issued to Jackson, one of the present inventors, on May 9, 1989 ("Jackson"), discloses host range, or "h-mutant," phages which attack phage-resistant strains of various plant bacteria, and methods of treating bacterially infected plants. The h-mutant phages, compositions containing such phages, and methods of treatment that are disclosed in Jackson are, however, limited to phages for plant bacteria and the treatment of plants infected with such bacteria.

Similarly, some measures have been taken to address the problem of bacterial diseases in humans, and to otherwise control and prevent bacterial growth. patent application Ser. No. 08/222,956 (the "'956 application"), which was published on Oct. 12, 1995 as WO 95/27043, discloses a type of phage therapy whereby mutant phage strains are introduced into a bacterially infected host. The mutant phages, which are thought to be resistant to degradation by the bacterially infected host's defense systems, particularly organs of the reticulo endothelial system, are believed to attack the harmful bacteria with which the host is infected. Thus, phages of the '956 application are believed to act as an in vivo antibacterial agent, and may be used either alone or as an adjunct to antibiotic therapy.

Although phages disclosed in the '956 application are introduced into bacterially infected hosts for the purpose of attacking undesirable bacteria, these phages included not only lytic, but also temperate viruses which are able to transfer pieces of donor bacterial DNA to recipient bacteria. Further, the '956 application lacks any disclosure that phages disclosed therein are able to attack, and thereby prevent or otherwise control the further growth of, phage-resistant bacterial strains.

Shortly after the discovery of phages as lytic agents of bacteria by Twort in 1915 and by d'Herelle in 1917, the investigation of their use for treating bacterial infections, which is typically referred to as phage therapy, began. Various phages are active against bacteria of many diseases in plants and animals, such as mammals. Phages that are active against bacteria which cause human diseases, such as anthrax, bronchitis, diarrhea, scarlet fever, typhus, cholera, diphtheria, gonorrhea, paratyphus, bubonic plague osteomyclitis, and other bacterially induced diseases, are known. While many in the art were initially convinced of the efficacy of phage therapy, particularly in controlling cholera, many phages were ineffective for in vivo treatment. It was believed that such ineffectiveness was due to the inactivation of phage by the host's immune system when administered parenterally, denaturation by gastric juices when taken orally, and the rapid emergence of phage-resistant bacterial mutants.

With the introduction and use of antibiotics, and their initial effectiveness in controlling bacterial diseases, much of the research for using phages as therapeutic agents ceased. Recently, phage therapy was successfully employed to treat nosocomial infections caused by antibiotic-resistant bacteria and certain opportunistic pathogens, namely, pyogenic infections and septicemias, especially staphylococcal, but also pseudomonads, enterobacteria (*E. coli, Klebsiella, Protius, Providencia, Serratia*), injuries (infected wounds and burns, postoperative infections, osteomyelitis), diseases of the skin and subcutaneous tissue (furunculosis, abscesses, acute lymphangitis, decubitus ulcers), urinary infections (chronic cystitis and pyelonephritis), respiratory diseases (sinusitis, mucopurulent bronchitis, pleuritis) and other diseases, for example, infantile diarrhea caused by enteropathogenic *E. coli* (7,8). In treating bacterial infections, phages may be administered orally in liquids, tablets and capsules, topically by aerosols and direct application, and intravenously. Phage therapy was conducted alone and in combination with antibiotics. Phages were also used as antiseptics, including uses such as disinfecting operating rooms, surgical instruments and lesions on patients, and medical care professionals.

Microorganisms such as bacteria can develop phage-resistant strains, however. Thus, phage therapy (or virus therapy for non-bacterial microorganisms) is somewhat undesirable from the standpoint that virus-resistant strains of a target strain of microorganism may persist in an infected host that is being treated, or in any other treated environment.

Conversely, many beneficial microorganism populations are threatened by viruses that will interfere with the beneficial properties of such microorganisms. Exemplary beneficial processes that are facilitated by microorganisms include industrial fermentation (e.g., in making food products), bioremediation of toxic chemicals, pollutants, and other undesirable substances, leaching of metals from low grade ores, extraction of petroleum and related products from shale, and drug manufacture. The efficiency of many beneficial processes is degraded by the ubiquitous nature of many viruses that will attack the microorganisms that facilitate these processes.

Thus, a need exists for an alternative method of controlling, reducing, or eliminating microorganism populations, which method addresses the ever-increasing emergence of antimicrobial resistance and the virus-resistance of microorganisms. A need also exists for a treatment which selects and destroys undesirable microorganisms while permitting beneficial microorganisms to survive. A need also exists for providing virus-resistant beneficial microorganisms.

SUMMARY

Although viruses have been used to control populations of microorganisms as previously described, many microorganisms can readily develop resistance to infection by viruses. Moreover, the use of temperate viruses in controlling populations of microorganisms is often ineffective since temperate viruses do not always proliferate in and lyse the infected host microorganisms.

"Wild-type" is defined herein as those viruses isolated from the wild or nature which display the most frequently observed phenotye, or physical characteristic, and is typically referred to as "normal." in contrast to "mutant." "Wild-type viruses" exhibit normal host-range virulence. "Wild-type microorganisms" do not resist infection by wild-type viruses specific for the particular target strain of microorganism.

"Host-range mutant viruses," which are also referred to as "h-mutant viruses," are defined herein as viruses which exhibit broader than normal host-range virulence. H-mutant viruses infect both wild-type microorganisms and virus-resistant variants of the target strain of microorganisms.

The invention thus includes one or more viruses which do not carry unwanted genes and are specific for one or more target strains of microorganisms. The viruses are lytic viruses which may be employed in processes including the control, reduction, or elimination of populations of a target strain of a microorganism. Preferably, a virus or virus mixture according to the present invention includes one or more h-mutant viruses. A mixture of one or more h-mutant viruses and one or more wild-type viruses is also within the scope of the present invention. Wild-type and h-mutant viruses "recognize" receptors on the surfaces of target strains, including one or more virus-resistant variant thereof, and infect these virus-resistant variants. Since the viruses of the present invention comprise lytic viruses, infected host cells will be lysed by the viruses. Viruses which are able to infect the wild-type of the target strain as well as a variety of virus-resistant variants of the target strain are preferred.

The h-mutant viruses of the present invention may be generated by isolating a wild-type of a target strain of a microorganism and growing this wild-type in the presence of a wild-tye virus which is specific for the target strain. Virus-resistant variants of the target strain will grow in the presence of the wild-type virus. The virus-resistant variants of the target strain are isolated and then grown in the presence of wild-type virus in order to generate h-mutant viruses. H-mutant virus-resistant variants of the target strain may then be obtained in a similar manner to the generation of virus-resistant variants of the target strain. These h-mutant virus-resistant variants may then be grown in the presence of h-mutant viruses in order to generate secondary h-mutants which will infect one or more virus-resistant variants of the target strain, imparting these h-mutants with a broader host range than their predecessors.

The invention also includes the virus-resistant and h-mutant virus-resistant variants of the microorganism, which are generated as described previously, and as hereinafter further described.

The viruses of the present invention may then be employed in a method of controlling, reducing, or eliminating populations of target strain microorganisms. The method includes introducing lytic viruses that are substantially devoid of undesirable genes into an environment where an undesirable target strain microorganism is present. As the target strain microorganism is exposed to the viruses, it is infected and eventually lysed. Since h-mutant viruses preferably infect wild-type and virus-resistant variants of the target strain, depending upon the concentration of h-mutant viruses, the preferred use of h-mutant viruses in the inventive method may effectively control, reduce, or eliminate the target strain microorganisms from the environment into which viruses are introduced.

In another aspect of the method of controlling populations of microorganisms includes introducing virus-resistant or h-mutant virus-resistant variants of a microorganism into an environment where the presence of the microorganism is desired. The introduction of such virus-resistant and h-mutant virus-resistant microorganisms is desirable in situations where the microorganism facilitates a beneficial process.

DETAILED DESCRIPTION

The present invention preferably includes host range-mutant lytic viruses, which are also referred to as h-mutant virulent viruses, or simply as h-mutant viruses, that infect and destroy virus-resistant strains of microorganisms. The present invention may also include wild-type lytic, or virulent, viruses, which are collectively referred to as "viruses" for simplicity. The viruses are preferably substantially free of undesirable genes. The present invention also includes a process for generating h-mutant viruses or mixtures of h-mutant and wild-type viruses that lack undesirable genes, such as genes that impart the virus with the ability to infect multicellular organisms, the ability to transfer undesirable genes to infected host microorganisms, and the ability to convert from a lytic state to a temperate state; a process for reducing, eliminating or otherwise controlling the growth of microorganism populations with h-mutant viruses or mixtures of h-mutant and wild-type viruses; and a process that utilizes h-mutant viruses or mixtures of h-mutant and wild-type viruses to generate virus-resistant and h-mutant virus-resistant strains of microorganisms. The virus-resistant and h-mutant virus-resistant strains of microorganisms that are generated by the inventive process are also within the scope of the present invention.

H-Mutant Viruses

The h-mutant viruses of the present invention are lytic, or virulent, viruses, which infect host microorganisms, utilize the various components of the host microorganisms to replicate and assemble progeny, and destroy the host, target strain microorganisms. Preferably, the h-mutant viruses of the present invention lack undesirable characteristics, including, without limitation, the ability to infect multicellular organisms, the ability to transfer undesirable genes to infected host microorganisms, and the ability to convert from a lytic state to a temperate state.

The viruses include an outer protein coat, or "capsid," which is capable of "recognizing" a receptor, or receptor site, on the outer surface of a target strain microorganism, including some receptors which have been altered, or "mutated," to impart the target strain microorganism with resistance to wild-type viruses or resistance to one or more h-mutant viruses. The ability of h-mutant viruses to recognize mutated receptors of the target strain microorganism enables h-mutant viruses to infect virus-resistant variations of the target strain microorganism.

Due to their ability to "recognize" receptors on the target strain microorganism, viruses of the present invention specifically infect the target strain, and do not infect other, non-targeted strains of a same species of microorganism, other non-targeted microorganisms, or other non-targeted cells. Thus, the inventive viruses are not as likely to inhibit the activity of beneficial microorganisms as antimicrobial drugs, which lack the specificity of viruses for a target microorganism.

When employed in a treatment method according to the present invention, as more fully described below, the inventive viruses proliferate as they destroy target strain microorganisms, reducing the need for repeated dosing in treatment, which includes the administration of viruses. In contrast, antimicrobial therapies require repeated doses since antimicrobial concentrations decrease during treatment.

After target strain microorganism populations are reduced or eliminated such that target strains are no longer present for the viruses to infect, the viruses become inactive, and will eventually be degraded. Following their degradation, the various components of the viruses may be utilized by other organisms as nutrients.

The process of generating h-mutant viruses of the present invention includes isolating virus-resistant microorganisms, and growing the virus-resistant microorganisms in the presence of wild-type viruses in order to generate and isolate h-mutant viruses.

A target strain of a microorganism is isolated by techniques which are known in the art. The target strain may then be identified or otherwise analyzed by known processes. Virus-resistant members of the target strain are then isolated by culturing the target strain in a medium that facilitates growth, or proliferation, of the target strain. Preferably, target strain microorganisms are grown on a sterilized, semi-solid medium, such as an agar. The target strain is grown in the presence of a wild-type virus that is capable of infecting the former. The concentration of the wild-type virus depends upon the desired MOI. Preferably, the relative concentrations of target strain microorganisms to wild-type viruses are about one-to-one, for an MOI of about one. Due to their ability to resist infection by the wild-type virus or otherwise survive a virus infection, some of the target strain microorganisms will grow in the presence of the wild-type virus. Such microorganisms are referred to as wild-type virus-resistant microorganisms, and will grow on the agar as "colonies." Thus, wild-type virus-resistant microorganisms may be isolated in the form of colonies by culturing target strain microorganisms in the presence of a wild-type virus that will infect, or is specific for, the target strain.

H-mutant viruses may then be generated and isolated by transferring a sample of the wild-type virus-resistant microorganism from a "colony" on agar, to a liquid or semi-solid growth medium that includes a high concentration of wild-type viruses. Thus, the MOI is preferably greater than one. The concentration of wild-type virus-resistant microorganisms will preferably facilitate growth of a confluent layer, which is also typically referred to as a "lawn," in a semi-solid growth medium. Although many of the viruses will have no effect on wild-type virus-resistant microorganisms, some mutants will infect and lyse the virus resistant microorganisms. These viruses are the h-mutants, and are isolated within substantially transparent areas of the lawn, which are typically referred to as "plaques."

The processes of isolating virus-resistant target strain microorganisms and generating, selecting, and isolating h-mutant viruses may be repeated in order to increase the range of virus-resistant microorganisms of a target strain that the hi-mutant viruses will infect. Such a process may be performed by growing virus-resistant microorganisms in the presence of h-mutant viruses rather than wild-type viruses. Alternatively, various h-mutants with different host ranges may be generated and isolated by conducting these processes several different times.

Screening for Undesirable Genes

After the viruses have been isolated, the presence or absence of undesirable genes (e.g., genes for virulence factors, toxins and antibiotic resistance) may be determined by comparison techniques that are known to those in the art, such as conventional agarose gel electrophoresis, pulsed-field gel electrophoresis, or use of nucleic acid hybridization probes. Such techniques include hybridization of any undesirable genes with complementary polymerase chain reaction (PCR)-amplified strands of DNA which include known undesirable genes (e.g., genes that impart the virus with the ability to infect multicellular organisms, the ability to transfer undesirable genes to infected host microorganisms, and the ability to convert from a lytic state to a temperate state). Hybrids may then be detected by known techniques, such as radio-assays.

As an example of such comparative screening, since the viruses of the present invention include only lytic viruses, temperate viruses will be screened by comparing the genes of these viruses to known genes that impart viruses with temperate characteristics. Temperate h-mutant viruses may then be excluded from virus mixtures of the present invention and from use in treatment methods of the present invention.

Temperate wild-type viruses may be screened and excluded in similar fashion from viruses and virus mixtures of the present invention. As previously identified, temperate viruses may transfer undesirable characteristics to a host target strain of a microorganism. Moreover, temperate viruses do not readily destroy the target strain microorganism. Thus, the use of temperate viruses in controlling, reducing or eliminating microorganism populations is not as desirable as the use of lytic viruses for these purposes.

The virus-resistant microorganisms that are generated in the foregoing process may be screened for other undesirable characteristics, such as antibiotic resistance, in a similar fashion.

Following screening for undesirable genes, viruses of the present invention which lack undesirable characteristics may then be proliferated and utilized in virus mixtures of the present invention, and in accordance with methods of the present invention.

Proliferating H-Mutant and Wild-Type Viruses

A process for proliferating the viruses of the present invention includes growing large quantities of the target strain microorganisms, including one or more virus-resistant variations thereof. The desired virus or viruses, such as one or more h-mutant variations or one or more wild-type variations of each desired virus, are then introduced into the presence of the target strain of microorganism at a desired MOI. An exemplary growth chamber comprises a bioreactor, into which nutrients may be continually introduced and from which microorganisms and/or viruses may be continually removed. The virus or viruses may also be proliferated in sterilized liquid growth medium in large flasks, or otherwise as known in the art.

Concentration and Storage of H-Mutant Viruses, Wild-Type Viruses and Virus-Resistant Microorganisms The viruses or virus mixtures may be concentrated by methods that are known in the art, such as chemical precipitation and ultrafiltration. Another method of concentrating h-mutant viruses includes isolating and concentrating infected, non-lysed target strain host microorganisms, which are referred to as "carriers." The use of carriers is desirable because a single carrier will eventually be lysed by viruses growing therein, and during lysis release a large number of viruses. In addition, it is easier to concentrate carrier microorganisms by conventional method, such as centrifugation, than it is to concentrate viruses by many conventional methods. Preferably, carriers are avirulent variations of the target strain microorganism, so that little or no risk exists of introducing a virulent target strain into a virus treatment site.

Viruses and carrier microorganisms of viruses may be stored as known in the art (e.g., by refrigeration at about 4° C., freezing or lyophilization processes) prior to use in the process of the invention. Alternatively, the viruses and carriers including the viruses of the present invention may be employed in accordance with a process of the present invention and/or concentration thereof.

The virus-resistant microorganisms of the present invention may be concentrated and/or stored in a manner, that is similar to the processes for concentrating and storing the viruses.

Stored or unstored viruses and virus mixtures, and virus-resistant microorganisms may then be utilized in accordance with the microorganism population control processes of the present invention, examples of which are set forth in detail below.

Methods of Microorganism Population Control

A. Use of Virulent Viruses to Control Microorganism Populations

A first embodiment of the inventive method includes employing viruses or virus mixtures of the present invention to control populations of target strain microorganisms. This first embodiment includes introducing the inventive viruses into a treatment site in order to lyse target strain microorganisms.

Foods or food products, such as raw meat and poultry, are exemplary treatment sites. The undesirable microorganisms that are typically present in raw meat and poultry treatment sites include, without limitation, the genera *Salmonella*, *Campylobacter*, and *Escherichia* (e.g., *E. coli*.) An exemplary target strain of *E. coli* is the infamous strain designated O157:H7. Introducing viruses that will infect and lyse undesirable microorganisms into raw meat and poultry treatment sites includes, but is not limited to, introducing the viruses into food and water of live animals, applying viruses to the living spaces of such animals, applying and otherwise introducing viruses to animal carcasses, meat, and surfaces in meat packing plants, storage and transportation containers, markets, and homes. Applying viruses to meat and poultry reduces or eliminates populations of undesirable microorganisms, which are thought to reduce or eliminate the incidences of disease and food spoilage caused by such microorganisms. Similarly, vegetation and other food products may be treated with the inventive viruses to control an increase in populations of undesirable microorganisms thereon.

Another exemplary treatment site into which the viruses may be introduced includes living animals (such as mammals, e.g., humans), or "subjects." The inventive viruses may be employed in the prevention (i.e., prophylaxis) or treatment (i.e., therapy) of diseases that are caused by a target strain of microorganism. Treatment and prophylaxis both include introducing the viruses into the subject by a known method. The viruses are preferably orally administered by a known enteral dosage form. The viruses may be topically administered in various known forms, such as aerosols, liquids, creams, lotions, soaps, powders, and salves. The viruses of the present invention may also be administered in accordance with processes that are known in the art, such as those disclosed in WO95/27043, the disclosure of which is hereby incorporated by reference in its entirety.

While being used in therapy of microbial infections, the viruses of the present invention may be introduced alone or in combination with one or more antibiotics, which are also referred to herein as "antimicrobial agents" or "bacteriocins."

The term "bacteriocin" was coined for antibacterial agents that are synthesized by bacteria and require specific receptors on the target microorganism. Various antibiotics and other antimicrobial agents are known in the art (see, e.g., Handbook of Antimicrobial Therapy, The Medical Letter (1984), the disclosure of which is hereby incorporated by reference in its entirety). The viruses of the present invention are especially useful for preventing infection by and treating antibiotic-resistant strains of bacteria.

The inventive viruses may also be employed to disinfect a target strain of a microorganism from an object. In disinfection, a composition including the viruses is applied to the object and the viruses lytically infect the target strain. Exemplary objects which may be disinfected in this manner include, but are not limited to, infected areas of healthcare facilities, operating rooms and treatment rooms in healthcare facilities, and equipment that is used by healthcare professionals.

Plant diseases that are caused by microorganisms may also be treated in accordance with this first embodiment of the method. The viruses that will infect target strains of plant disease-causing or harmful, e.g., ice-nucleation, microorganisms may be applied to infected or contaminated plants, seedlings, seeds, or soil or other matter which supports the foregoing by spraying or introduction into the plant's water supply. As an example of the treatment of plants, legume seed may be treated with a virus or virus mixture that will infect and lyse undesirable strains of rhizobia that are present in soil, and that will not infect beneficial strains of rhizobia. The virus, which preferably includes an h-mutant virus, will reduce or eliminate undesirable rhizobia strains, while the desirable rhizobia strains will benefit the plant as the plant grows.

The first embodiment of the method of the present invention may also be employed to control microorganism populations that are detrimental to the environment. As an example, the inventive viruses may be employed to reduce populations of microorganisms which deplete oxygen from bodies of water, and permit an increase of oxygen levels in these waters. Nutrients from sewage and fertilizer that are introduced into pond water, river water, or sea water can create algal blooms. The algae eventually die and are then decomposed by various microorganisms, which proliferate and continue decomposing the dead algae. During proliferation of such microorganisms, oxygen is depleted from the water, which inhibits growth of most other organisms therein. The introduction of viruses that infect and lyse specific algae species which may form blooms at a particular site would control the populations of such algae microorganisms and, therefore, the formation of algal blooms, thereby permitting oxygen levels in the water to increase, and facilitating reintroduction of other types of life into these previously oxygen-depleted treatment sites.

As another example of this method, viruses of the present invention may be employed to reduce the occurrence of "acid mine drainage," which is an environmental problem associated with coal mining. *Thiobacillus ferrooxidans*, a bacterial species that oxidizes iron sulfide, is a major cause of acid mine drainage. As acidic mine drainage pollutes the water in nearby lakes, rivers and streams, the quality of these waters deteriorates. Acid and metals that are dissolved in acid mine drainages are toxic to aquatic life and render the water unsafe for consumption and human activity. The introduction of viruses that will infect and lyse *T. ferrooxidans* would therefore be useful in reducing or eliminating this type of bacteria from coal mines, and reduce the occurrence of acid mine drainage.

The control, reduction, and elimination of pathogenic agents is another example of this method of the invention. Exemplary pathogenic agents include, but are not limited to, various types of bacterial (e.g., *Bacillus anthracis, Salmonella typhi, Vibrio cholerae, Yersina pestis, Xanthomonas albilineans, A. campestris* pv. *citri*, and *X. campestris* pv. *oryzae*) rickettsial (e.g., *Coxiella burnetii* and *Rickettsia prowazeki*), and fungal organisms. The dissemination of inventive viruses that infect and lyse such pathogenic agents into treatment sites where such pathogenic agents are present would control, reduce, and potentially eliminate populations of such pathogenic agents.

The first embodiment of the process of the present invention may also be employed to selectively control, reduce or eliminate populations of undesirable microorganisms that inhibit the ability of beneficial microorganisms to perform beneficial processes. As those of skill in the art are aware, several types of microorganisms, which are referred to as beneficial microorganisms or beneficial agents, benefit their hosts. The ability of a beneficial microorganism to benefit its host may, however, be interfered with by an undesirable microorganism. A preferred virus or virus mixture that would be useful in treating a target strain of undesirable microorganisms in accordance with the first embodiment of the process would infect and lyse the target strain, and would not infect or lyse any of the beneficial microorganisms.

Similarly, the bioremediation of toxic chemicals by beneficial microorganisms may be interfered with by undesirable target strains of microorganisms. For example, pseudomonads, which produce a variety of antimicrobial substances, may be present in a mixture of bioremediating microorganisms. The presence of antimicrobial substances in such mixtures, however, is undesirable since it may destroy the ability of many of the microorganisms to bioremediate toxic chemicals. Accordingly, the viruses of the present invention would be useful in the present method for controlling the number of undesirable antimicrobial-producing microorganisms in such a mixture.

Other microorganisms are beneficial for some purposes, but may be detrimental in other regards. One such microorganism, *P. aeruginosa* occurs naturally in soil, and is useful in the bioremediation of many environmental pollutants. *P. aeruginosa*, however, also causes various diseases in plants and animals. Thus, this method of the invention would be useful for controlling, reducing, or eliminating the population of *P. aeruginosa* after that microorganism has performed its beneficial task.

Populations of genetically engineered microorganisms may be controlled, reduced, or eliminated in a similar manner. Since many people fear that the use of genetically engineered microorganisms for beneficial purposes may also have adverse effects, the elimination of such genetically engineered microorganisms may be desirable. Thus, viruses that infect and lyse a target strain of genetically engineered microorganism may be utilized in accordance with this embodiment of the invention to control, reduce, or eliminate populations of genetically engineered target strain microorganisms from a treatment site following their use for beneficial purposes.

B. Methods of Using Virus-Resistant Microorganisms to Control Microorganism Populations As described previously, many beneficial microorganisms, or "beneficial agents," perform beneficial processes. Such microorganisms, however, are susceptible to being infected and lysed by viruses. Accordingly, a second embodiment of the method of the present invention includes the use of virus-resistant strains of beneficial microorganisms in beneficial processes.

Virus-resistant microorganisms are generated, as previous described, by growing a target strain of microorganism in the presence of wild-type and/or h-mutant viruses that will infect and lyse the target strain microorganism. Virus-resistant microorganisms may then be isolated as discussed previously, and proliferated in a growth medium under otherwise substantially sterile and preferably controlled conditions.

As an example of the use of the second embodiment of the process, virus-resistant *Pantoeca ananus*, which is parasitic for the rust fungi, *Puccinia* spp., is useful for controlling the growth of rust fungus on wheat. Phages which attack *P. ananus* are, however, also present in proximity to the rust fungus, and have a detrimental effect on the ability of *P. ananus* to control rust fungus. Accordingly, the application of virus-resistant strains of *P. ananus* to wheat would be useful in controlling the growth of rust fungus on the wheat. Similarly, the application of virus-resistant *P. ananus* to rust fungus-infected wheat would be useful for preventing the spread of rust fungus to other wheat plants, and for treating the rust fungus-infected wheat plants.

Similarly, some bacteria, such as *Serratia entomaphilia*, control the proliferation and spread of insect populations, such as New Zealand grass grub, or *Costelytra zealandica*, and may be applied to treat plants or to prevent the spread of such insects to other plants. Other virus-resistant bacteria used for biological pest control, such as *Enterobacter aerogenes* for locusts, are also useful in the second embodiment of the process of the present invention.

Other beneficial microorganisms are useful for performing processes which include, without limitation, leaching in order to oxidize the sulfide of sulfide-rich minerals to sulfuric acid so as to liberate and concentrate valuable minerals, such as copper and uranium, from low-grade ores (i.e., *T. ferrooxidans* and *Acidiphiliium* spp.); releasing petroleum and related substances from bituminous shale (e.g., *Rhodococcus* spp., *Stlfobus* spp., and/or *Thiobacillus* spp.); acidifying sulfur or other matter to acidify alkaline soils that have been selected for agricultural uses (e.g., *Rhodococcus* spp., *Sulfobus* spp., and/or *Thiobacillus* spp.); decomposing tires and other rubber products for recycling (e.g., *Rhodococcus* spp., *Sulfobus* spp., and/or *Thiobacillus* spp.); bioremediation of hazardous chemicals and pollutants (e.g., *Rhodococcus* spp., *Sulfobus* spp., and/or *Thiobacillus* spp.); treatment of wastewater discharges and sludges in which other microorganisms produce foul-smelling odors (e.g., from dairy and hog farms, kennels, farms, etc.); and in industrial fermentation processes (e.g. lactic acid bacteria for the production of cheese). The use of virus-resistant microorganisms in such processes in accordance with the second embodiment of the process of the present invention reduces the likelihood that the beneficial microorganisms will be infected or lysed by viruses specific therefor.

Although the invention has been described with regard to certain preferred embodiments, the scope of the invention is to be defined by the appended claims and their legal equivalents.

What is claimed:

1. A method of controlling a population of a target strain of a microorganism on a food, comprising:
   introducing a virus composition into contact with a food that has been at least partially prepared for consumption, the food possibly contaminated with a target strain of a host microorganism,
   the target strain of the host microorganism comprising a microorganism that causes a disease state in humans or animals or a microorganism that causes food to spoil,
   the virus composition comprising variant virus particles, the variant virus particles having an expanded host range over a wild-type virus particle, the expanded host range including:
      a wild-type of the target strain of the host microorganism; and
      at least one virus-resistant variation of the target strain of the host microorganism that resists infection by the wild-type virus particle; and
   permitting the variant virus particles to bind to and infect:
      the wild-type of the target strain of the host microorganism; and
      the at least one virus-resistant variation of the target strain of the host microorganism
   to limit growth of a population of the wild-type of the target strain of the host microorganism and the at least one virus-resistant variation of the target strain of the host microorganism.

2. The method according to claim 1, wherein introducing the virus composition comprises introducing the virus composition in which the variant virus particles are lytic virus particles.

3. The method according to claim 1, wherein introducing the virus composition comprises introducing the virus composition including wild-type virus particles into contact with the food.

4. The method according to claim 1, further comprising:
   introducing an antimicrobial agent into a treatment site at which the food is present.

5. The method according to claim 1, wherein introducing the virus composition comprises introducing the virus composition into contact with raw meat or raw poultry.

6. The method according to claim 1, wherein introducing the virus composition comprises introducing the virus composition in which variant virus particles are selective for the target strain microorganism over a beneficial microorganism.

7. The method according to claim 1, wherein introducing comprises introducing the virus composition into contact a food possibly contaminated with *E. coli* 0157:H7.

8. A method for disinfecting a food at least partially prepared for a human or an animal to consume, comprising:
   applying a virus composition to a food at least partially prepared for consumption by a human or an animal, the virus composition comprising variant virus particles:
      being specific for a target strain of a host microorganism comprising a microorganism that causes a disease state in the human or the animal or a microorganism that causes food to spoil; and
      having an expanded host range over a wild-type virus particle, the expanded host range of the variant virus particles including:
         a wild-type of the target strain of the host microorganism; and
         at least one virus-resistant variation of the target strain of the host microorganism that resists infection by the wild-type virus particle; and
   permitting the variant virus particles to bind to and infect:
      the wild-type of the target strain of the host microorganism; and
      the at least one virus-resistant variation of the target strain of the host microorganism to limit growth of a population of the target strain of the host microorganism, including the wild-type of the target strain and the at least one virus-resistant variation of the target strain.

9. The method according to claim 8, wherein applying comprises applying the virus composition to a food comprising at least one of raw meat and raw poultry.

10. A method for disinfecting meat or poultry to be consumed by a human or an animal, comprising:
applying a virus composition to meat or poultry to be consumed by a human or an animal, the virus composition comprising variant virus particles:
being specific for a target strain of a host microorganism comprising a microorganism that causes a disease state in the human or the animal or a microorganism that causes food to spoil; and
being selected for an inability to transfer undesired genes to the target strain of the host microorganism upon infecting the target strain of the host microorganism; and
having an expanded host range over a wild-type virus particle, the expanded host range including:
a wild-type of the target strain of the host microorganism; and
at least one virus-resistant variation of the target strain of the host microorganism that resists infection by the wild-type virus particle; and
permitting the variant virus particles to bind to and infect:
the wild-type of the target strain of the host microorganism; and
the at least one virus-resistant variation of the target strain of the host microorganism
to limit growth of a population of the wild-type of the target strain of the host microorganism and the at least one virus-resistant variation of the target strain of the host microorganism.

11. The method according to claim 10, wherein applying comprises applying the virus composition to the meat or poultry to kill, prevent growth of or prevent proliferation of the target strain of a host microorganism comprising a bacteria from at least one of the *Salmonella* genus, the *Campylobacter* genus, and the *Escherichia* genus.

12. The method according to claim 10, wherein applying comprises applying the virus composition to the meat or poultry to kill, prevent growth of or prevent proliferation of the target strain of a host microorganism comprising *E. coli* 0157:H7.

13. The method according to claim 10, wherein applying comprises applying the virus composition to raw meat or raw poultry.

14. The method according to claim 8, wherein applying comprises applying the virus composition to the food to kill, prevent growth of or prevent proliferation of the target strain of a host microorganism comprising a bacteria from at least one of the *Salmonella* genus, the *Campylobacter* genus, and the *Escherichia* genus.

15. The method according to claim 8, wherein applying comprises applying the virus composition to the food to kill, prevent growth of or prevent proliferation of the target strain of a host microorganism comprising *E. coli* 0157:H7.

* * * * *

UNITED STATES PATENT AND TRADEMARK OFFICE
CERTIFICATE OF CORRECTION

PATENT NO. : 8,821,855 B2  Page 1 of 1
APPLICATION NO. : 12/027209
DATED : September 2, 2014
INVENTOR(S) : Jackson et al.

It is certified that error appears in the above-identified patent and that said Letters Patent is hereby corrected as shown below:

In the Specification

Column 3, Line 13, insert a --,-- after "loaf"

Column 3, Line 37, change "Shigellaspecies" to --Shigella species--

Column 3, Lines 54 and 55, insert a --,-- after "hospitals"

Column 4, Line 3, change "VEEF" to --VREF--

Column 6, Line 50, change "patent" to --Patent--

Column 8, Line 45, change "wild-tye" to --wild-type--

Column 10, Line 62, change "hi-mutant" to --h-mutant--

Column 13, Line 28, italicize "rhizobia"

Column 15, Line 4, change "previous" to --previously--

Signed and Sealed this
Twenty-fifth Day of November, 2014

Michelle K. Lee
*Deputy Director of the United States Patent and Trademark Office*